United States Patent
Patel et al.

(10) Patent No.: US 11,141,359 B2
(45) Date of Patent: Oct. 12, 2021

(54) ANHYDROUS COSMETIC COMPOSITION

(71) Applicant: L'OREAL, Paris (FR)

(72) Inventors: Sonal Patel, Iselin, NJ (US); Balanda Atis, Newark, NJ (US)

(73) Assignee: L'OREAL, Paris (FR)

( * ) Notice: Subject to any disclaimer, the term of this patent is extended or adjusted under 35 U.S.C. 154(b) by 92 days.

(21) Appl. No.: 15/941,459

(22) Filed: Mar. 30, 2018

(65) Prior Publication Data
US 2019/0298623 A1   Oct. 3, 2019

(51) Int. Cl.
| | | |
|---|---|---|
| *A61K 8/02* | (2006.01) | |
| *A61K 8/58* | (2006.01) | |
| *A61K 8/81* | (2006.01) | |
| *A61K 8/894* | (2006.01) | |
| *A61K 8/92* | (2006.01) | |
| *A61Q 19/00* | (2006.01) | |
| *A61K 8/892* | (2006.01) | |

(52) U.S. Cl.
CPC ............ *A61K 8/0241* (2013.01); *A61K 8/585* (2013.01); *A61K 8/8147* (2013.01); *A61K 8/892* (2013.01); *A61K 8/894* (2013.01); *A61K 8/922* (2013.01); *A61Q 19/00* (2013.01); *A61K 2800/31* (2013.01)

(58) Field of Classification Search
None
See application file for complete search history.

(56) References Cited

U.S. PATENT DOCUMENTS

| | | |
|---|---|---|
| 6,027,738 A | 2/2000 | Stepniewski et al. |
| 6,103,250 A | 8/2000 | Brieva et al. |
| 6,960,339 B1 * | 11/2005 | Ferrari .................. A61K 8/042 424/63 |
| RE39,218 E | 8/2006 | Mellul et al. |
| 2005/0187128 A1 * | 8/2005 | Martin .................... A61K 8/19 510/392 |
| 2006/0013790 A1 | 1/2006 | Shimizu |
| 2008/0305068 A1 * | 12/2008 | Zheng .................... A61K 8/891 424/78.03 |
| 2016/0166479 A1 * | 6/2016 | Chiou .................... A61K 8/064 514/785 |

FOREIGN PATENT DOCUMENTS

EP   1068856 A1 *   1/2001   ............ A61K 8/042

OTHER PUBLICATIONS

Chris Deziel, How to Convert from Centistokes to Centipoise, at https://sciencing.com/convert-centistoke-centipoise-8279085.html (updated Mar. 13, 2018) (Year: 2018).* https://www.skinstore.com/dermablend-flawless-creator-liguid-foundation-drops-30ml-various-shades/11527835.html, accessed Aug. 30, 2019, pp. 1-2.

https://www.dermablend.com/poresaver-matte-makeup-primer/3606000525399.html, accessed Aug. 30, 2019, pp. 1-2.

* cited by examiner

*Primary Examiner* — David J Blanchard
*Assistant Examiner* — Sarah J Chickos
(74) *Attorney, Agent, or Firm* — Oblon, McClelland, Maier & Neustadt, L.L.P.

(57) ABSTRACT

The present disclosure relates to anhydrous cosmetic composition comprising hydrophobic silica particles, PMMA particles, silicone oil, hydrocarbon oil, silicone elastomer and silicone emulsifier.

18 Claims, 1 Drawing Sheet

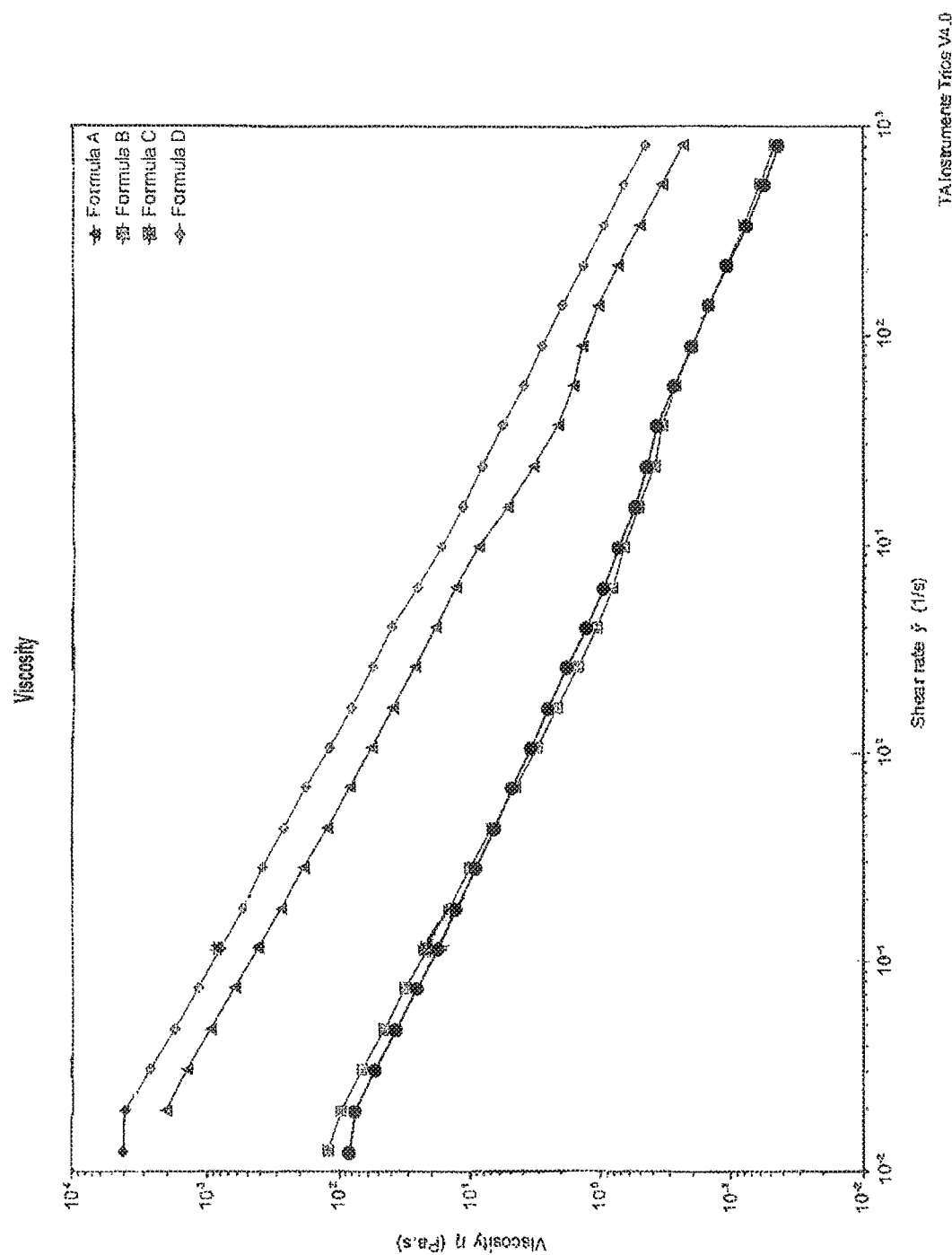

ANHYDROUS COSMETIC COMPOSITION

FIELD OF THE DISCLOSURE

The present invention relates to anhydrous compositions and to the uses of such compositions, in particular in the cosmetic and/or dermatological fields.

BACKGROUND

In the field of cosmetic compositions, it is known to use soft-focus minerals or organic fillers that absorb sebum and perspiration, in order to achieve various benefits (for example, skin mattifying or smoothness).

However, the use of these materials are sometimes accompanied by a dry, rough feel and lack of comfort that is unacceptable for the user.

Silicone elastomers are also widely used as mattifying agents because also tend to provide a soft feel on the skin. However, they must be used at a relatively high content in order to have the mattifying effect, and these may create dry and coarse (i.e. cakey) texture.

Accordingly, there is still a need for cosmetic compositions that have mattifying effects on the skin, and which have good properties, in particular which are soft on application. Moreover, the inventors of the instant invention have recognized that a sensation of comfort during application and a silky skin feel after skin penetration are desired.

SUMMARY OF THE INVENTION

One aspect of the present invention pertains to a cosmetic composition, comprising: hydrophobic silica particles; at least 10 percent of PMMA particles; a silicone oil; a hydrocarbon oil; a silicone elastomer; a silicone emulsifier; and wherein the composition is anhydrous.

Another aspect of the present invention pertains to a cosmetic composition, comprising: hydrophobic silica particles; PMMA particles; a silicone oil; a hydrocarbon oil; a silicone elastomer; a silicone emulsifier; and wherein the viscosity of composition is between about 10 Pa·s. and about 1000 Pa·s. when measured at a shear rate of 1 $s^{-1}$, wherein the composition is anhydrous.

FIGURE

FIG. 1 shows a graph of the viscosities of anhydrous cosmetic compositions consistent with embodiments of the invention and of comparative compositions.

DETAILED DESCRIPTION OF THE INVENTION

As used herein, the terms "comprises", "comprising," "having," and "including" are used in their open, non-limiting sense.

The terms "a," "an," and "the" are understood to encompass the plural as well as the singular. Thus, the term "a combination thereof" also relates to "combinations thereof." Throughout the disclosure, the term "a mixture thereof or combination thereof" is used, following a list of elements as shown in the following example where letters A-F represent the elements: "one or more elements selected from the group consisting of A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from the group consisting of A, B, C, D, E, F, and a combination of any two or more of A, B, C, D, E, and F."

The term "INCI" is an abbreviation of International Nomenclature of Cosmetic Ingredients, which is a system of names provided by the International Nomenclature Committee of the Personal Care Products Council to describe personal case ingredients.

The term "active weight" refers to the amount of a particular ingredient exclusive of any solvent, carrier, impurities and the like that may be supplied with particular ingredient.

The term "solid basis" or "solid content" means considering only components (e.g., in a composition) that are solid at room temperature and ignoring portions of the composition that are liquid, e.g., water and other volatile solvents.

The expression "one or more" means "at least one" and thus includes individual components as well as mixtures or combinations.

Other than in the operating examples, or where otherwise indicated, all numbers expressing quantities of ingredients and/or reaction conditions are to be understood as being modified in all instances by the term "about," meaning within +/−5% of the indicated number.

The term "anhydrous" as used herein means that there is less than about 2% by weight of water added to a composition, based on the total weight of the composition. Nonetheless, the compositions may include less than about 1 wt. %, less than about 0.5 wt. % less than about 0.1 wt. %, or none at all.

All percentages, parts and ratios herein are based upon the total weight of the compositions of the present invention, unless otherwise indicated.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material.

The term "copolymer" as used herein refers to polymers formed from at least two different types of monomers.

The term "pigment" as used herein means any colored and/or iridescent mineral or organic particles that are insoluble in the liquid hydrophilic phase, which are intended to color and/or add iridescence to the composition.

According to the present invention, the inventors have found that anhydrous cosmetic composition of the present invention has a unique silky, "air-like" texture. The high solid content in the present invention optimizes soft focus effect on skin by enhancing the matte finish. The composition enhances the degree of matte finish by absorbing the excess oil or sebum from the skin while reducing the shine without drying skin, in certain embodiments it does that by maintaining the natural appearance of the skin tone.

Hydrophobic Silica Particles

The composition according to the present invention comprises hydrophobic silica particles.

The hydrophobic silica may be fumed (i.e., may be a "fumed silica"). The fumed silica may be obtained by modifying the surface of the silica via a chemical reaction that generates a reduction in the number of silanol groups, these groups possibly being substituted especially with hydrophobic groups.

The fumed silica is also known as pyrogenic silica, it is produced in a flame and generally consists of microscopic droplets of amorphous silica fused into branched, chainlike, three-dimensional secondary particles which then agglomerated into tertiary particles. The resulting powder has an extremely low bulk density and high surface area.

The hydrophobic groups may be:
a. trimethylsiloxyl groups, which may be obtained by modifying the surface of the silica via the presence of hexamethyldisilazane. Silicas thus treated are known as "Silica silylate" according to the CTFA (8th edition, 2000). They are sold, for example, under the references VM-2270 AEROGEL by the company Dow Corning.
b. dimethylsilyloxyl or polydimethylsiloxane groups, which are especially obtained by treating fumed silica in the presence of polydimethylsiloxane or dimethyldichlorosilane. Silicas thus treated are known as "Silica Dimethyl Silylate" according to the CTFA (8th Edition, 2000). They are sold, for example, under the references AEROSIL R972 and AEROSIL R974 by the company Degussa, and CAB-O-SIL TS-610 and CAB-O-SIL TS-720 by the company Cabot.

In general, the hydrophobic silica particles are present in an amount that is sufficient to adjust the hardness of the compositions according to the invention to the required value.

In certain embodiments, the hydrophobic silica particles may be fumed.

In one embodiment, the hydrophobic fumed silica particles are in the form of a white, free flowing powder. The particles are completely hydrophobic providing a vehicle for thickening oil phase materials, reducing the volatility of many volatile fluids and the absorption of may lipophilic materials including sebum.

According to certain embodiments of the invention, the hydrophobic fumed silica particles have a porosity greater than 90%, white, free-flowing, powder having bulk density of 40-100 kg/m$_3$, average particle size 5-15 microns, surface area 600-800 m$_2$/g.

An example of suitable hydrophobic fumed silica particles is those from Dow corning under the trade name VM-2270 AEROGEL.

The concentration of hydrophobic silica particles may be present in a composition in accordance with the invention in a content ranging from about 0.5%, 1%, or 2% to about 3%, 5%, or 10% by weight, including all ranges and subranges there between, all weights being based on the total weight of the composition.

PMMA Particles

The PMMA (also known as poly (methylmethacrylate)) particles useful in the composition of the present invention are formed from polymerizing methyl methacrylate.

In certain embodiments of the present invention PMMA particles may be identified as methyl methacrylate crosspolymer or crosslinked poly methyl methacrylate.

Methyl methacrylate crosspolymer is synthetic copolymer of methyl methacrylate and may be crosslinked with glycol dimethacrylate. It has the empirical formula:

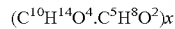

$(C^{10}H^{14}O^4.C^5H^8O^2)x$ and has been assigned Chemical Abstracts Service (CAS) No. 25777-71-3. It is also described at page 808, volume 1, *International Cosmetic Ingredient Dictionary and Handbook* (Seventh Edition, 1997), published by The Cosmetic, Toiletry, and Fragrance Association (Washington, D.C.).

An example of a methyl methacrylate crosspolymer is available from Sekisui Plastics Co., Ltd. under the trade name TECHPOLYMER MBP-8. The product specifications of the TECHPOLYMER MBP-8 include: porous spherical particles, white powder having an average micropore diameter of 8 µm, surface area of 85 m$^2$/g, oil absorption 140 ml/100 g, high oil absorption and pleasant to touch.

Methyl methacrylate crosspolymers are also commercially available from Nihon Junyaku under the trade name JURYMER MB-1P, from Sensient Cosmetic Technologies under the trade name COVABEAD LH 85, from Ganz Chemical Co., Ltd. Under the trade name GANZPEARL GMP-0800 and from Tomer under the trade name MICROSPHERE M-305.

The inventors have found according to certain embodiments, by including at least about 10% of PMMA particles provides enhanced aesthetic and stability of the composition. In certain embodiments the concentration is from about 10%, 12%, 14%, or 15% to about 16%, 18%, 20% or 25% including all ranges and subranges there between, all weights being based on the total weight of the composition.

Silicone Oils

The term "silicone oil" means an oil comprising at least one silicon atom, and especially comprising Si—O groups. The silicone oil(s) may be volatile or non-volatile.

As used herein, by "oils" or "oil" it is meant compounds having a melting point of less than about 30° C. and generally insoluble in water and includes a hydrophobic moiety, such as one meeting one or more of the following three criteria: (a) has a carbon chain of at least six carbons in which none of the six carbons is a carbonyl carbon or has a hydrophilic moiety (defined below) bonded directly to it; (b) has two or more alkyl siloxy groups; or (c) has two or more oxypropylene groups in sequence. The hydrophobic moiety may include linear, cyclic, aromatic, saturated or unsaturated groups. The hydrophobic compound is in certain embodiments not amphiphilic and, as such, in this embodiment does not include hydrophilic moieties, such as anionic, cationic, zwitterionic, or nonionic groups, that are polar, including sulfate, sulfonate, carboxylate, phosphate, phosphonate, ammonium, including mono-, di-, and trialkylammonium species, pyridinium, imidazolinium, amidinium, poly(ethyleneiminium), ammonioalkylsulfonate, ammonioalkylcarboxylate, amphoacetate, and poly(ethyleneoxy) sulfonyl moieties. In certain embodiments, the oil does not include hydroxyl moieties.

In certain embodiments, the silicone oil that may be used in the present invention may be chosen from silicone oils with a flash point ranging from 40° C. to 150° C., preferably with a flash point of greater than 55° C. and less than or equal to 105° C., and preferentially ranging from 65° C. to 95° C. The flash point is measured in particular according to standard ISO 3679.

The term "volatile" refers to a compound that can evaporate on contact with the skin in less than one hour, at room temperature and atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10"3 to 300 mmHg), preferably ranging from 1.3 Pa to 13 000 Pa (0.01 to 100 mmHg) and preferentially ranging from 1.3 Pa to 1300 Pa (0.01 to 10 mmHg).

In certain embodiments, the volatile silicone oils that may be mentioned include cyclopolydimethylsiloxanes (INCI name: cyclomethicone), such as cyclopentasiloxane, cyclohexasiloxane, octylmethylcyclotetrasiloxane, decamethylcyclopentasiloxane, dodecamethylcyclohexasiloxane; linear silicones such as heptamethylhexyltrisiloxane, heptamethyloctyltrisiloxane, hexamethyldisiloxane, octamethyltrisiloxane, decamethyltetrasiloxane and dodecamethylpentasiloxane.

In certain embodiments, the silicone oil may be chosen from linear or cyclic silicone oils, such as linear or cyclic polydimethylsiloxanes (PDMSs), which are liquid or pasty at room temperature, especially cyclopolydimethylsiloxanes (cyclomethicones) such as cyclohexasiloxane; polydimethyl-siloxanes comprising alkyl, alkoxy or phenyl groups, which are pendent or at the end of a silicone chain, these groups containing from 2 to 24 carbon atoms, phenyl silicones, for instance phenyl trimethicones, phenyl dimethicones, phenyltrimethylsiloxydiphenyl-siloxanes, diphenyl dimethicones, diphenylmethyl-diphenyltrisiloxanes or 2-phenylethyl trimethylsiloxy silicates, and polymethylphenylsiloxanes, combinations thereof.

Preferably, the silicone oil is chosen from polymethylsiloxane and phenyl polymethylsiloxane.

The concentration of silicone oils may be present in a composition in accordance with the invention in a content ranging from about 30%, 32%, 36%, 40%, or 45% to about 50%, 52%, 55%, 58%, 62%, or 65% by weight, including all ranges and subranges there between, all weights being based on the total weight of the composition.

Hydrocarbon Oils

The term "hydrocarbon oil" means an oil formed essentially from or even constituted of, carbon and hydrogen atoms, and optionally oxygen and nitrogen atoms, and not containing any silicon or fluorine atoms. Oils may contain for example, alcohol, ester, ether, carboxylic acid, amine and/or amide groups.

In certain embodiments, the hydrocarbon-based oils that may be used in the composition of the present invention, examples that may be mentioned include:

synthetic esters and ethers, especially of fatty acids, for instance the oils of formulae R1COOR2 and R1OR2 in which R1 represents a fatty acid residue containing from 8 to 29 carbon atoms and R2 represents a branched or unbranched hydrocarbon-based chain containing from 3 to 30 carbon atoms, for instance purcellin oil, isononyl isononanoate, isopropyl myristate, isopropyl palmitate, 2-ethylhexyl palmitate, 2-octyldodecyl stearate, 2-octyldodecyl erucate or isostearyl isostearate, hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; and pentaerythritol esters, for instance pentaerythrityl tetraisostearate;

hydrocarbon-based oils of plant origin, such as perhydrosqualene, liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, almond oil, apricot oil, macadamia oil, arara oil, coriander oil, castor oil, avocado oil, caprylic/capric acid triglycerides, jojoba oil, shea butter oil, meadowfoam oil and argan oil;

volatile or non-volatile, linear or branched hydrocarbons, of mineral or synthetic origin, and derivatives thereof, such as liquid petroleum jelly and hydrogenated polyisobutene such as PARLEAM oil, C8-Ci6 branched alkanes or isoalkanes (also known as isoparaffins), isododecane, isodecane, isohexadecane, for instance the isoparaffins sold under the trade name ISOPAR by the company Exxon Chemical or the oils sold under the trade name PERMETHYL by the company Presperse; and combinations thereof;

linear alkanes, especially of plant origin, preferably comprising from 7 to 14 carbon atoms;

fatty alcohols that are liquid at room temperature, containing from 8 to 26 carbon atoms, for instance octyldodecanol, 2-butyloctanol, 2-hexyldecanol, 2-undecylpentadecanol or oleyl alcohol.

The concentration of hydrocarbon oils may be present in a composition in accordance with the invention in a content ranging from about 20%, 22%, 26%, 30%, or 35% to about 38%, 40%, 44%, 48% or 50% by weight, including all ranges and subranges there between, all weights being based on the total weight of the composition.

Silicone Elastomers

The term "organopolysiloxane elastomer" or "silicone elastomer" means a supple, deformable organopolysiloxane with viscoelastic properties and especially with the consistency of a sponge or a supple sphere. It is more particularly a crosslinked organopolysiloxane elastomer. The elastomer is advantageously a non-emulsifying elastomer, i.e. an organopolysiloxane elastomer not containing any hydrophilic chains, and in particular not containing any polyoxyalkylene units (especially polyoxyethylene or polyoxypropylene) or any polyglyceryl units.

In particular, the silicone elastomer used in the present invention may be chosen from Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name).

In certain embodiments, the organopolysiloxane elastomer is in form of particles and may be conveyed in the form of a gel constituted of an elastomeric organopolysiloxane included in at least one hydrocarbon-based oil and/or one silicone oil. Non-emulsifying elastomers are especially described in patents EP 242 219, EP 285 886 and EP 765 656 and in patent application JP-A-61-194 009.

Mention may be made especially of the compounds having the following INCI names:

Dimethicone/Vinyl Dimethicone Crosspolymer, such as USG-105 and USG-107A from the company Shin-Etsu; DC9506 and DC9701 from the company Dow Corning;

Dimethicone/Vinyl Dimethicone Crosspolymer (and) Dimethicone, such as KSG-6 and KSG-16 from the company Shin-Etsu;

Dimethicone/Vinyl Dimethicone Crosspolymer (and) Cyclopentasiloxane, such as KSG-15;

Cyclopentasiloxane (and) Dimethicone Crosspolymer, such as DC9040, DC9045 and DC5930 from the company Dow Corning;

Dimethicone (and) Dimethicone Crosspolymer, such as DC9041 from the company Dow Corning;

Dimethicone (and) Dimethicone Crosspolymer, such as Dow Corning EL-9240 Silicone Elastomer Blend from the company Dow Corning (mixture of polydimethylsiloxane crosslinked with hexadiene/polydimethylsiloxane (2 cSt));

C4-24 Alkyl Dimethicone/Divinyl Dimethicone Crosspolymer, such as NULASTIC SILK MA from the company Alzo;

Dimethicone/Vinyl Dimethicone Crosspolymer (and) Dimethicone, such as KSG-6 and KSG-16 from the company Shin-Etsu;

Dimethicone (and) Dimethicone Crosspolymer, such as DC9041 from the company Dow Corning;

Dimethicone (and) Dimethicone Crosspolymer, such as Dow Corning EL-9240 Silicone Elastomer Blend from the company Dow Corning (mixture of polydimethylsiloxane crosslinked with hexadiene/polydimethylsiloxane (2 cSt));

Dimethicone (and) Dimethicone Crosspolymer, such as Dow Corning EL-9241DM Silicone Elastomer Blend from the company Dow Corning; and the combination of polydimethylsiloxane crosslinked with hexadiene/polydimethylsiloxane (5 cSt) sold under the name DC 9041 by Dow Corning.

In certain embodiments, the organopolysiloxane elastomer particles may also be used in powder form: mention may be made especially of the powders sold under the names Dow Corning 9505 Powder and Dow Corning 9506 Powder by the company Dow Corning, these powders having the INCI name: Dimethicone/Vinyl Dimethicone Crosspolymer. The organopolysiloxane powder may also be coated with silsesquioxane resin, as described, for example, in U.S. Pat. No. 5,538,793. Such elastomeric powders are sold under the names KSP-100, KSP-101, KSP-102, KSP-103, KSP-104 and KSP-105 by the company Shin-Etsu, and have the INCI name: vinyl Dimethicone/Methicone Silsesquioxane Crosspolymer.

The concentration of silicone elastomers may be present in a composition in accordance with the invention in a content ranging from about 0.01%, 0.5%, 1%, or 3% to about 4%, 6%, or 7% by weight, including all ranges and subranges there between, all weights being based on the total weight of the composition.

Silicone Emulsifiers

In certain embodiments, useful emulsifiers for the composition of the present invention are those with an HLB (hydrophilic-lipophilic balance) no greater than 7. Although any cosmetically acceptable emulsifier with an HLB no greater than 7 can be used in the compositions, excellent results can be obtained using silicone based emulsifiers (sometimes referred to herein as "silicone emulsifier"). Examples of some useful silicone emulsifiers are: (1) dimethicone and PEG/PPG-18/18 dimethicone (e.g., X-22-6711D from Shin-Etsu); (2) dimethicone and dimethicone crosspolymer (e.g., Dow Corning 9041 Silicone Elastomer Blend); (3) dimethicone and dimethicone/PEG-10/15 crosspolymer (KSG-210 from Shin-Etsu); and (4) dimethicone and dimethicone/polyglycerin-3 crosspolymer (KSG 710 from Shin-Etsu).

In certain embodiments, the silicone emulsifier that may be used in the present invention may be chosen from polyether substituted linear or branched polysiloxane copolymers. One particular co-emulsifier is PEG-10 dimethicone available under the tradename of ES-5612 from Dow Corning Corporation (Midland, Mich.), or KF-6017 from Shin-Etsu (Akron, Ohio). Another preferred co-emulsifier is dimethicone (and) PEG/PPG-18/18 dimethicone available under the tradename of ES-5226 DM from Dow Corning Corporation (Midland, Mich.) Other suitable co-emulsifiers include, PEG-9 polydimethylsiloxyethyl dimethicone available under the tradename KF-6028 and PEG-9, lauryl PEG-9 polydimethylsiloxyethyl dimethicone available under the tradename KF-6038, both available from Shin-Etsu (Akron, Ohio).

The concentration of silicone emulsifier may be present in a composition in accordance with the invention in a content ranging from about 0.1%, 1%, 3%, or 5% to about 6%, 8%, or 10% by weight, including all ranges and subranges there between, all weights being based on the total weight of the composition.

Additional Ingredients

The composition of the present invention is substantially free of water.

In certain embodiments, composition of the present invention is free of pigments, including white pigments, opacifiers, or colored pigments.

One skilled in art will recognize that color pigments are included to impart color in the present composition.

According to one or more embodiments of the present invention, compositions may further comprise at least one coloring agent are provided. The types of pigments that are employed can be organic, including natural colorants and synthetic monomeric and polymeric colorants.

According to one or more embodiments, the at least one coloring agent may be chosen from pigments, dyes, nacreous pigments, and pearling agents.

The pigments can also be inorganic; inorganic pigments include iron oxides (yellow, red, brown or black), ferric ammonium ferrocyanide(blue), manganese violet, ultramarine blue, chrome oxide(green), talc, lecithin modified talc, zeolite, kaolin, lecithin modified kaolin, titanium dioxide (white), zinc oxide and mixtures thereof. Also useful are transparent metal oxide-coated silica beads. Metal oxides, particularly iron and titanium oxides, are the most common color components of makeups, particularly foundations and concealers. However, one of the primary advantages of the present system is that it permits the creation of a highly effective concealer without the presence of large amounts of metal oxide pigments, which render the makeup heavier and more opaque, and thus leave the skin looking somewhat unnatural.

While in certain embodiments, compositions of the present invention include pigments in a content ranging from about 0.1%, 1%, 3%, or 5% to about 6%, 8%, or 10% by weight, including all ranges and subranges there between, all weights being based on the total weight of the composition. However, in certain other embodiments, compositions of the present invention are substantially free of coloring agents.

The compositions may also benefit from the incorporation of one or more plate-like, non-spherical powders that confer some luster, but not an overt shine.

Examples of such powders include, but are not limited to, bismuth oxychloride, boron nitride, barium sulfate, mica, sericite, muscovite, synthetic mica, titanium oxide coated mica, titanium oxide coated bismuth oxychloride, titanium oxide coated talc, platelet iron oxides, metal powders such as aluminum, lauroyl lysine and platelet talc, to the extent these materials.

These powders, when used, are essentially present as fillers, and therefore may make up the bulk of the remainder of the product outside the essential and preferred components named above, and therefore the amount may be any amount needed to make up the remainder of the composition According to preferred embodiments of the present invention, the compositions of the present invention further may include wax. As used herein, "wax" is intended to mean a lipophilic fatty compound that is solid at room temperature (about 25° C.) and atmospheric pressure (760 mm Hg, i.e., 105 Pa), which undergoes a reversible solid/liquid change of state and which has a melting point of greater than 30° C., and in some embodiments, greater than about 55° C. up to about 120° C. or even as high as about 200° C.

The term wax may include waxes of animal origin, waxes of plant origin, waxes of mineral origin and waxes of synthetic origin. Examples of waxes of animal origin include beeswaxes, lanolin waxes and Chinese insect waxes. Examples of waxes of plant origin include rice waxes, carnauba wax, candelilla wax, ouricurry wax, cork fiber waxes, sugar cane waxes, Japan waxes, sumach wax and cotton wax. Examples of waxes of mineral origin include paraffins, microcrystalline waxes, montan waxes and ozokerites. Examples of waxes of synthetic origin include polyolefin waxes, e.g., polyethylene waxes, waxes obtained by Fischer-Tropsch synthesis, waxy copolymers and their esters, and silicone and fluoro waxes.

The term wax may further include high melting point hydrogenated oils of animal or plant origin. Examples include hydrogenated jojoba waxes and hydrogenated oils which are obtained by catalytic hydrogenation of fats composed of a $C_8$-$C_{32}$ linear or nonlinear fatty chain, hydrogenated sunflower oil, hydrogenated castor oil, hydrogenated copra oil, hydrogenated lanolin and hydrogenated palm oils.

While in certain embodiments, compositions of the present invention include pigments in a content ranging from about 0.1%, 1%, 3%, or 5% to about 6%, 8%, or 10% by weight, including all ranges and subranges there between, all weights being based on the total weight of the composition. However, in certain other embodiments, compositions of the present invention are substantially free of wax.

The composition of the present invention may be made by mixing two phases, solid phase and anhydrous liquid phase. In certain embodiments solid phase of the present invention may be dissolved, dispersed or suspended in the anhydrous liquid phase.

According to the present invention solid basis of the composition comprises hydrophobic fumed silica particles, PMMA particles, silicone elastomers and silicone emulsifier. The anhydrous liquid phase of the composition comprises silicone oil and hydrocarbon oil.

The concentration of the solid basis in a composition in accordance with the invention is including at least about 15%. In certain embodiments the concentration is from about 15%, 17%, 20%, or 22% to about 24%, 26%, 28%, 30% or 35% including all ranges and subranges there between, all weights being based on the total weight of the composition.

In certain embodiments, the present cosmetic composition comprises of hydrophobic silica particles, PMMA particles, silicone elastomers and silicone emulsifier are present in a combined concentration by weight that is at least about 15 percent.

The cosmetic composition of the present invention may further include various additives desirably used in cosmetic or dermatological compositions. For example, fragrances, pearlescent agents, colorants, particulates, thickeners, dispersants, anti-oxidants, pH adjusters, preservatives, neutralizing agents, fragrances, fillers, co-solvents, plasticizers, cosmetic and dermatological active agents such as emollients, moisturizers, vitamins, UV filters, and sunscreens, and combinations thereof can be added. A non-exhaustive listing of such ingredients can be found in the CTFA *International Cosmetic Ingredient Dictionary and Handbook*, Fourteenth Edition (2012), contents of which are incorporated herein by reference in its entirety.

One skilled in the art will take care to select the optional additional additives and/or the amount thereof such that the advantageous properties of the mascara compositions according to the present invention are not, or are not substantially, adversely affected by the envisaged addition.

These substances may be selected variously by one skilled in the art to prepare a composition which has the desired properties, for example, consistency or texture.

Examples

TABLE 1

| INCI US | Inventive | | Comparative | |
| --- | --- | --- | --- | --- |
| | Formula A | Formula D | Formula B | Formula C |
| SILICA SILYLATE | 1.1 | 1.8 | 0.5 | 0.5 |
| METHYL METHACRYLATE CROSSPOLYMER | 11 | 15 | 8 | 5 |
| PEG-10 DIMETHICONE | 3.5 | 3.5 | 3.5 | 3.5 |
| DIMETHICONE | 37.4 | 32.7 | 55 | 51 |
| DIMETHICONE (and) DIMETHICONE CROSSPOLYMER | 20 | 20 | 17 | 20 |
| ISODODECANE | 27 | 27 | 16 | 20 |
| Total | 100 | 100 | 100 | 100 |

The viscosity of the various formulas were compared. The viscosities were measured using the TA Instruments Trios V4.0. Compared to the comparative formulas in the FIG. 1, the inventive formulas have the viscosity between about 10 Pa·s and about 1000 Pa·s. when measured at a shear rate of 1 $s^{-1}$. This viscosity range promotes a pleasant skin feel, easy application to the skin, and product stability.

Compared to the comparative formulas in the Table 1, the inventive formulas showed a very good adherence to the skin which absorbs the excess oil or sebum form skin while reducing shine without drying skin and maintain natural skin tone. Additionally, the high solid content in the formula optimizes soft focus effect enhancing the flawless matte finish. It also, improves the texture of skin by reducing stickiness, tackiness.

Compositions of the present invention can be worn alone or along other makeup products such as moisturizer, primer, over makeup or blended with other beauty products. It can also be applied underneath or on top of these products.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. accordingly, the description is not intended to limit the invention to the form disclosed herein. Also, it is intended to the appended claims to construed to include alternative embodiments.

What is claimed:

1. A cosmetic composition, comprising: hydrophobic silica particles;
   at least about 10 percent by weight of the composition of polymethylmethacrylate (PMMA) particles;
   a silicone oil, wherein the silicone oil is present in an amount from about 35 percent to about 60 percent by weight of the composition;
   a hydrocarbon oil, wherein the hydrocarbon oil is present in an amount from about 22 percent to about 40 percent by weight of the composition;
   a silicone elastomer;
   and a silicone emulsifier;
   wherein the composition is anhydrous and has a liquid phase.

2. The cosmetic composition of claim 1 wherein the hydrophobic silica particles are present in a concentration by weight that is from about 0.01 percent to about 4 percent of the composition.

3. The cosmetic composition of claim 1 wherein the hydrophobic silica particles are silica silylate particles.

4. The cosmetic composition of claim 1 wherein the PMMA particles are present in a concentration by weight that is from about 10 percent to about 18 percent of the composition.

5. The cosmetic composition of claim 1 wherein the silicone oil is selected from a group consisting of a polymerized siloxane, polydimethylsiloxane, cyclo siloxanes, and combinations thereof.

6. The cosmetic composition of claim 1 wherein the hydrocarbon oil is selected from a group consisting of plant based oils, synthetic ethers, mineral oil, synthetic esters, alkane hydrocarbon, and combinations thereof.

7. The cosmetic composition of claim 1 where in the composition is substantially free of wax.

8. The cosmetic composition of claim 1 wherein the silicone elastomer is present in a concentration by weight that is from about 0.01 percent to about 5 percent of the composition.

9. The cosmetic composition of claim 1 wherein the silicone elastomer is selected from a group consisting of polyether dimethicone crosspolymers, polyether silicone elastomers, polyglyceryl silicone elastomers, and combinations thereof.

10. The cosmetic composition of claim 1 wherein the silicone emulsifier is present in a concentration by weight that is from about 0.1 percent to about 8 percent of the composition.

11. The cosmetic composition of claim 1 wherein the silicone emulsifier is selected from a group consisting of polyglyceryl silicone, dimethicone copolyol, and combinations thereof.

12. The cosmetic composition at claim 1 wherein the hydrophobic silica particles, PMMA particles, silicone elastomers and silicone emulsifier are present in a combined concentration by weight that is at least about 15 percent of the composition.

13. A cosmetic composition, comprising:
    hydrophobic silica particles;
    polymethylmethacrylate (PMMA) particles;
    a silicone oil, wherein the silicone oil is present in an amount from about 35 percent to about 60 percent by weight of the composition;
    a hydrocarbon oil, wherein the hydrocarbon oil is present in an amount from about 22 percent to about 32 percent by weight of the composition;
    a silicone elastomer; and
    a silicone emulsifier; wherein the composition is anhydrous.

14. The cosmetic composition of claim 13 wherein the hydrophobic silica particles, PMMA particles, silicone elastomers and silicone emulsifier are present in a combined concentration by weight that is at least about 10 percent of the composition.

15. A cosmetic composition, comprising: hydrophobic silica particles;
    at least about 10 percent by weight of the composition of polymethylmethacrylate (PMMA) particles;
    a silicone oil wherein the silicone oil is resent in an amount from about 35 percent to about 60 percent by weight of the composition;
    a hydrocarbon oil, wherein the hydrocarbon oil is present in an amount from about 22 percent to about 38 percent by weight of the composition;
    a silicone elastomer;
    and a silicone emulsifier;
    wherein the composition is anhydrous and has a viscosity.

16. The cosmetic composition of claim 1, wherein the hydrocarbon oil is a volatile hydrocarbon oil.

17. The cosmetic composition of claim 13, wherein the hydrocarbon oil is a volatile hydrocarbon oil.

18. The cosmetic composition of claim 15, wherein the hydrocarbon oil is a volatile hydrocarbon oil.

* * * * *